| United States Patent [19] | | [11] | Patent Number: | 4,478,840 |
|---|---|---|---|---|
| Smith, Jr. | | [45] | Date of Patent: | Oct. 23, 1984 |

[54] APPETITE SUPPRESSING COMPOSITIONS AND METHODS

[75] Inventor: Dewey H. Smith, Jr., Wilmington, Del.

[73] Assignee: E. I. Du Pont de Nemours and Company, Wilmington, Del.

[21] Appl. No.: 540,763

[22] Filed: Oct. 11, 1983

[51] Int. Cl.$^3$ .......................................... A61K 31/485
[52] U.S. Cl. .................................................. 424/260
[58] Field of Search ........................................ 424/260

[56] References Cited

U.S. PATENT DOCUMENTS

| 3,393,197 | 7/1968 | Pachter | 260/285 |
| 3,814,768 | 6/1974 | Fishman | 260/285 |
| 3,896,226 | 7/1975 | Fishman | 424/260 |
| 4,141,897 | 2/1979 | Olofson | 546/45 |
| 4,161,597 | 7/1979 | Olofson | 546/15 |
| 4,217,353 | 8/1980 | Smith | 424/260 |
| 4,322,426 | 3/1982 | Hermann | 424/260 |
| 4,366,159 | 12/1982 | Magruder | 424/260 |

FOREIGN PATENT DOCUMENTS

| 1442 | 2/1964 | Japan . |
| 6683 | 5/1964 | Japan . |
| 22189 | 10/1965 | Japan . |
| 3702 | 3/1966 | Japan . |

OTHER PUBLICATIONS

Am. J. Hosp. Pharm., 37, 942–9, (1980), Miller.
J. Rosenblatt and S. Stencel, "Weight Control-A National Obsession", 1982, Congressional Quarterly, vol. II, No. 19, 855 et seq.
S. G. Holtzman, "Behavioral Effects", J. Pharmacol. Exp. Ther., vol. 189, 51–60, (1974).
S. G. Holtzman, "Effects of Narcotics Antagonists", Life Sciences, vol. 16, 1465–70, (1975).
R. Bognar, et al., "Chiroptical Properties", Collection Czech. Chem. Commun., vol. 40, 670, (1975).
Seki, "N-Phenethyl-14-hydroxynormorphine Derivatives, CA 64: 3626 g, (1966).
Seki, "14-Hydroxyhydrodeoxymorphine-D", CA 56:8777a, (1962).
CAS ONLINE Computer-based information search, CAS Registry Compounds, 75752-05-5 and 75768-7-2-8.

Primary Examiner—Douglas W. Robinson

[57] ABSTRACT

Compositions of certain 17-cycloalkylmethyl-4,5α-epoxymorphinan-3,14-diol compounds are useful for suppression of appetite in mammals.

12 Claims, No Drawings

APPETITE SUPPRESSING COMPOSITIONS AND METHODS

TECHNICAL FIELD

This invention relates to compositions containing certain 17-cycloalkylmethyl-4,5α-epoxymorphinan-3,14-diol compounds such as 17-cyclopropylmethyl-4,5α-epoxymorphinan-3,14-diol, and to a method of use of such compositions and compounds to suppress appetite in mammals.

BACKGROUND OF THE INVENTION

At any given time, a large segment of the U.S. population is on a "serious" diet to lose weight for either medical or psychological/cosmetic reasons. As judged by the number of "recommended" diets, dieting publications, exercise regimens, and weight loss preparations, there is no universally acceptable method to reduce weight. Weight control has therefore evolved into a very large industry in the United States with consumer spending of about $10 billion annually. J. Rosenblatt and S. Stencel, "Weight Control—A National Obsession," 1982 Congressional Quarterly, Vol. II, No. 19, 855 et seq. Currently, the prevalent social view of obesity is conditioned by cosmetic considerations which shifts to medical considerations only when weight gain becomes extreme. Rosenblatt and Stencel, page 4, supra; "Slimming Food," Mintel Publications, December 1982.

Severe dieting can also lead to extreme weight loss, possibly inducing the condition known as anorexia nervosa in which many victims starve themselves to death. Existing pharmacological means for weight loss and weight control, such as amphetamines, are powerful habit-forming drugs with dangerous side effects, and other drugs for this purpose are either ineffective or dangerous. Rosenblatt and Stencel, supra. There is a need for safe and efficacious compositions and methods to control weight.

U.S. Pat. No. 4,217,353 issued to Smith on Aug. 12, 1980, discloses that the narcotic antagonist, naltrexone ((−)-17-cyclopropylmethyl-4,5α-epoxy-3,14-dihydroxymorphinan-6-one), can be administered orally to effect appetite suppression in mammals. Holtzman, *J. Pharmacol. Exp. Ther.*, 189, 51–60 (1974), has shown that the narcotic antagonist naloxone (N-allyl-14-hydroxy-7,8-dihydronormorphinone) suppresses eating by food-deprived rats but not by food-deprived mice. In a subsequent study, Holtzman showed that the fluid intake (sweetened Enfamil TM baby formula) of rats was reduced following subcutaneous administration of naloxone, naltrexone or nalorphine (N-allylnormorphine); *Life Sciences*, 16, 1465–70 (1975).

Japanese Pat. No. 1442 (1964) to Sankyo describes an analgesic compound of the formula:

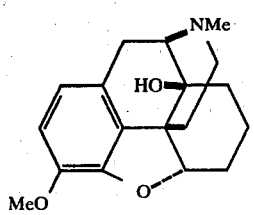

Japanese Pat. No. 6683 (1964) to Sankyo describes an analgesic compound of the formula:

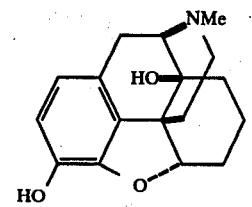

The N-methyl compound:

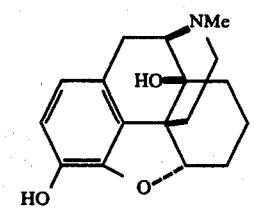

is also listed in CAS-OnLine TM as "references not available"; the corresponding O-methyl compound is mentioned in Bognar et al., *Collect. Czech. Chem. Commun.*, 40 (3), 670–680 (1975), where it was studied as part of an investigation of circular dichroism.

Japanese Pat. No. 1443 (1964) to Sankyo describes narcotic antagonists of the formula:

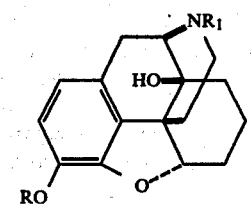

where R=H or Me and $R_1$=allyl or propargyl.

Japanese Pat. No. 3625 (1966) to Sankyo describes antipyretic and antitussive compounds of the formula:

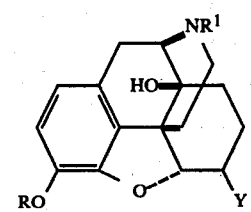

where R=lower alkyl or aralkyl; and Y is H, oxo, OH, etc.

Japanese Pat. No. 3702 (1966) to Sankyo describes analgesic and antitussive compounds of the formula:

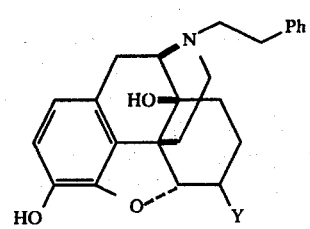

where R is lower alkyl; and Y=ketone, α- or β-OH, H, or ethylenedioxy.

Japanese Pat. No. 40-22189 (1965) to Sankyo claims an O-demethylation reaction producing

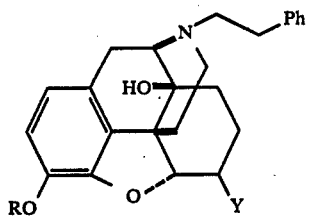

where Y=oxo, α- or β-OH, or H. Where Y=H, the 17-phenethyl compound and its HCl salt are specifically described.

Olofson et al., U.S. Pat. No. 4,141,897, describes compounds related to those of the subject case as substrates for an N-dealkylation method. All bear protecting groups on the 3- and 14-hydroxy groups. (Claim 1) Corresponding N-acylated or N-nor compounds are described in Olofson et al., U.S. Pat. No. 4,161,597.

A pending application, U.S. Ser. No. 437,324, filed Oct. 28, 1982, claims use of nalbuphine (17-cyclobutylmethyl-4,5α-epoxymorphinan-3,6α,14-triol) and nalmefene (former USAN, nalmetrene; 17-cyclopropylmethyl-4,5α-epoxy-6-methylenemorphinan-3,14-diol) as anorectics.

Such hydroxy opiate derivatives as those described above possess a diverse spectrum of activities, and there is no indication in the known art that the 17-cycloalkyl-methyl-4,5α-epoxy-morphinan-3,14-diols of this invention would be effective appetite suppressants.

The Chemical Abstracts Service CAS-OnLine ™ computer file does however, contain a record containing the following structures

|  | R | Reg. No. |
|---|---|---|
|  | CH$_2$—◁ | 75768-72-8 |
|  | CH$_2$—◇ | 75752-05-5 |

No information whatsoever, however, is listed with regard to the synthesis or possible utility of the compounds. The computer record merely notes "references not available."

SUMMARY OF THE INVENTION

At this time, a clear need exists for safe and reliable pharmaceutical compositions for weight control. The unexpected finding that the small number of compounds and compositions comprising the instant invention possess appetite suppressing properties is of major significance. Specifically, one aspect of this invention relates to an appetite suppression composition comprising an effective appetite suppressing amount of a compound of Formula I:

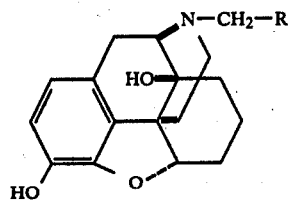

wherein R is cyclopropyl or cyclobutyl; or a pharmaceutically suitable salt thereof together with the suitable vehicles, or excipients, or mixtures thereof. The compositions are neither stimulant nor depressant, and are not expected to cause central nervous system excitement, sedation, hypothermia or other side effects at anorectic doses. Therefore they lack many of the disadvantages connected with other appetite suppressant compounds and compositions currently available. Preferred by virtue of their high activity, are the compositions incorporating the compound of Formula I wherein R is cyclopropyl or a pharmaceutically suitable salt thereof. Specifically preferred is 17-cyclopropylmethyl-4,5α-epoxymorphinan-3,14-diol, hydrochloride.

Another aspect of this invention relates to a method for suppressing appetite in a mammal which comprises administering to said mammal an effective appetite suppressing amount of a compound of Formula I:

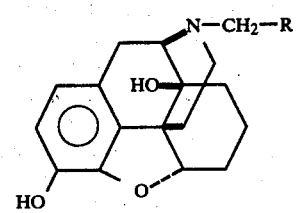

wherein R is cyclopropyl or cyclobutyl; or a pharmaceutically suitable salt thereof.

Another aspect of this invention relates to a method of improving the bodily appearance of a nonopiate-addicted mammal which comprises administering to said mammal an effective appetite suppressing dose of a compound of Formula I:

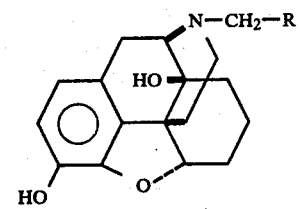

wherein R is cyclopropyl or cyclobutyl; or a pharmaceutically suitable salt thereof in a dosage effective to reduce appetite, and repeating said dosage until a cosmetically beneficial loss of body weight has occurred.

The compounds of this invention also possess other useful properties. For example, the compound of Formula I in which R is cyclobutyl is a mixed analgesic/narcotic antagonist; the compound of Formula I in which R is cyclopropyl is a narcotic antagonist.

The compounds of this invention, in causing a condition of appetite reduction, may be useful in an animal model for finding drugs to treat anorexia nervosa.

DETAILED DESCRIPTION OF THE INVENTION

The compounds of Formula I of this invention are prepared from the known 4,5α-epoxy-3-methoxymorphinan-14-ol, II, whose preparation is described by I. Seki, *Takamine Kenyusho Nempo*, 13, 67–74 (1961) [CA, 56, 8777 (1962)], and illustrated by Scheme I.

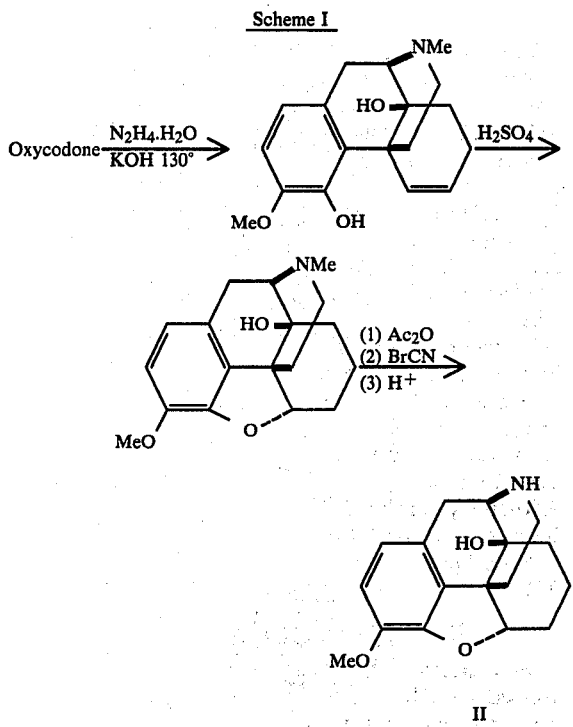

Further reaction of II as shown in Scheme II produces the desired compounds of Formula I, where R is defined as above.

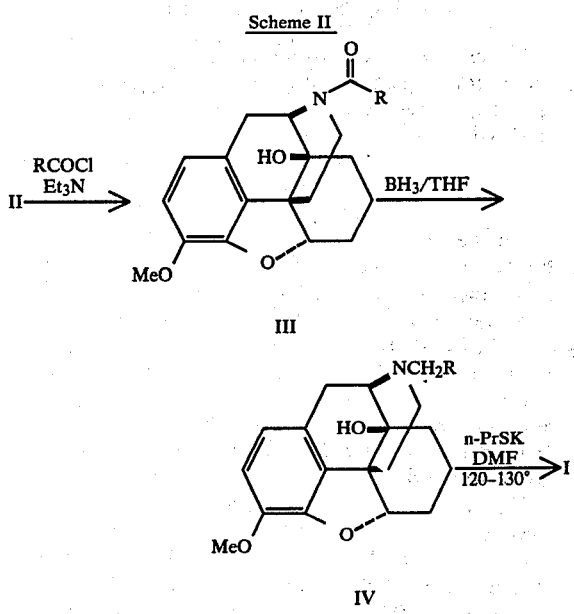

The amides III are prepared by reacting the secondary amine II with the appropriate acid chloride, such as cyclopropanecarbonyl chloride, in the presence of triethylamine or another base, organic or inorganic, to take up the hydrogen chloride generated in the reaction. The amide III is reduced to the amine IV using borane in tetrahydrofuran (THF). The ether functionality of IV was cleaved using propane thiolate in dimethylformamide. Other O-demethylation reagents, such as pyridine hydrochloride, may be used. The salts, such as the hydrochloride salt, are prepared by contacting with the appropriate acid, such as hydrogen chloride.

In this manner, one can prepare such salts as the hydrochloride, hydrobromide, neutral and acid sulfate, phosphate, nitrate, acetate, benzoate, salicyclate, neutral and acid fumarate and maleate, terephthalate, ethanesulfonate, bitartrate, and others.

The preparation of the compounds of this invention is described in detail in the following examples. All temperatures are reported in degrees centigrade.

EXAMPLE 1

17-Cyclopropylmethyl-4,5α-epoxymorphinan-3,14-diol, Hydrochloride

A. Acylation

To a suspension of 4,5α-epoxy-3-methoxymorphinan-14-ol [Seki, *Takamine Kenyusho Nempo*, 13, 67–74 (1961); Chem. Abst. 56, 8777 (1962)] (4.3 g) in 50 ml of chloroform, triethylamine (6 ml) was added, followed by 1.9 g of cyclopropanecarbonyl chloride. The reaction mixture was heated at reflux for one hour, diluted with more chloroform, and washed with excess 1N HCl to remove unreacted base, and then with water, dilute sodium bicarbonate, and water. The chloroform solution of the amide was dried over anhydrous magnesium sulfate, the inorganic salts filtered off, and the filtrate evaporated to yield an oil, which on trituration with hexane gave a solid (5.2 g), m.p. 125°–130°, 17-cyclopropylcarbonyl-4,5α-epoxy-3-methoxymorphinan-14-ol. Thin-layer chromatographic examination on silica gel (chloroform:ethanol, 85:15) indicated that the product was free from the starting material.

B. Reduction

The amide prepared as described above (1A) was dissolved in 50 ml of anhydrous tetrahydrofuran, and gradually added to an ice-cold solution of borane in tetrahydrofuran (80 ml; 0.96M $BH_3$). After the addition was complete, the reaction mixture was heated at reflux for 4 hours. The reaction mixture was cooled, and excess reagent decomposed by addition of 200 ml of 3N HCl. Then the organic solvent was removed by evaporation in vacuo, and the acidic solution heated at reflux for 6 hours. The acidic reaction mixture was cooled, basified with ammonia to pH 9.4, and the liberated alkaloid extracted with ether. The ether solution was then extracted with 40 ml of 2N HCl to convert the alkaloid back to the hydrochloride, and then converted to the pure base by the addition of dilute alkali. The organic base was extracted with ether, washed with water, dried over anhydrous potassium carbonate, the inorganic salts filtered off, and the ether evaporated to yield a gummy residue (3.5 g) of 17-cyclopropylmethyl-4,5α-epoxy-3-methoxymorphinan-14-ol.

C. O-Demethylation

The above obtained intermediate (1B) was dissolved in 90 ml of anhydrous dimethylformamide, and potassium tert-butoxide (4.5 g) was added, followed by 6 ml of 1-propanethiol. The reaction mixture was gradually heated in a current of nitrogen at 125°–130° for 3 hours. The reaction mixture was then cooled, and quenched by the addition of 5 ml of glacial acetic acid. The solvents were removed by evaporation under reduced pressure. The residue was treated with 20 ml of 2N HCl and extracted with ether to remove nonbasic material. The acidic extract was made basic to pH 9.4 by the addition of ammonia, the precipitated solids collected by filtration, washed thoroughly with water, and air dried. Recrystallization from methanol provided 2.7 g, m.p. 186°–188°, of 17-cyclopropylmethyl-4,5α-epoxymorphinan-3,14-diol.

Mass spectrum: $C_{20}H_{25}NO_3$ requires 327; observed, 327.

D. Hydrochloride Salt Formation

To twenty-five milliliters of 1N HCl, 1.1 g of the above obtained base (1C) was added and heated until solution was complete, and then cooled to room temperature. The precipitated hydrochloride salt was collected by filtration, dried at room temperature, and then in a vacuum oven at 75°–80° for 24 hours. The product, 17-cyclopropylmethyl-4,5α-epoxymorphinan-3,14-diol, hydrochloride, which seems to be hydrated, melts at 135°–136°.

EXAMPLE 2

17-Cyclobutylmethyl-4,5α-epoxymorphinan-3,14-diol, Hydrochloride

A. Acylation

To a suspension of 4,5α-epoxy-3-methoxymorphinan-14-ol, hydrochloride (8.4 g) in 100 ml of water, ammonium hydroxide was added to pH 10. The liberated free base was extracted with methylene chloride (500 ml), and then washed with water, the extract concentrated to low volume, and triethylamine (15 ml) added, followed by cyclobutanecarbonyl chloride (7 g). The reaction mixture was heated at reflux for 2 hours, cooled, treated with a slight excess of 2N HCl to remove unreacted base, and excess triethylamine. The methylene chloride solution was then washed with water, then dilute potassium carbonate solution, and finally with water. The solvent was then completely removed by evaporation, and the residue triturated with hexane to leave 17-cyclobutylcarbonyl-4,5α-epoxy-3-methoxymorphinan-14-ol, (7.5 g), m.p. 140°.

B. Reduction

The above described amide (2A) was dissolved in 100 ml of anhydrous tetrahydrofuran, and added to an ice-cold solution of borane in tetrahydrofuran (140 ml; 1M $BH_3$) and then heated at reflux for 6 hours. The reaction mixture was cooled, and excess reducing reagent decomposed by cautious addition of 20 ml of glacial acetic acid. Most of the tetrahydrofuran was removed by evaporation under reduced pressure; 60 ml of 6N HCl was then added, and the mixture heated at reflux for 16 hours. The reaction mixture was cooled, basified with alkali and extracted with methylene chloride. Evaporation of the methylene chloride layer provided a residue, which still contained the amide borane complex. The residue was dissolved in 200 ml of methanol, treated with 15 ml of 50% NaOH, and heated at reflux for 6 hours. The alcohol was then removed by evaporation, and the residue extracted with 600 ml of chloroform, washed with water, and the solvent evaporated. Thin-layer chromatographic examination on alumina indicated the presence of mainly one component. Infrared spectral examination showed no boron complex. The product was purified by column chromatography on basic alumina using as eluant a solvent system consisting of 95 parts chloroform and 5 parts ethanol. The yield of 17-cyclobutylmethyl-4,5α-epoxy-3-methoxymorphinan-14-ol was 6.5 g.

Mass Spectrum: $C_{22}H_{29}NO_3$ requires 355; found 355.

C. O-Demethylation

The above described 3-O-methyl ether (2B) was dissolved in 120 ml of anhydrous dimethylformamide. Potassium tertiary butoxide (6.1 g) was then added, followed by 7 g of n-propanethiol. The reaction mixture was gradually heated to 125°–130° in an atmosphere of nitrogen for a period of 2.5 hours. The reaction mixture was cooled to 20° and quenched by the addition of 6.5 ml of glacial acetic acid. The pH of the solution was almost neutral. The solvents were removed by evaporation under reduced pressure on a rotary evaporator. The residue was dissolved in 60 ml of 1N hydrochloric acid and extracted with 250 ml of ether to remove nonbasic materials. The acidic extract was then basified by the addition of ammonium hydroxide to pH 9.4. The crystalline product was collected by filtration, washed with water and dried in a vacuum oven at 80° for eighteen hours to provide 5.6 g of 17-cyclobutylmethyl-4,5α-epoxymorphinan-3,14-diol, (m.p. of non-recrystallized material 186°–188°).

Mass Spectrum: calcd. for $C_{21}H_{27}NO_3$: 341; found: 341.

D. Formation of Hydrochloride Salt

Five grams of the dried material from 2C above was treated with 100 ml of 3N HCl, heated until solution occurred, and cooled. The hydrochloride salt was collected by filtration, air dried, and then dried in a vacuum oven at 80° for 18 hours. The product, 17-cyclobutylmethyl-4,5α-epoxymorphinan-3,14-diol, hydrochloride, melted at 255°–260°; yield, 4.5 g.

ANOREXIA TEST PROCEDURES

The anorexigenic activities of the compositions of the instant invention are demonstrated by administering the agents to experimental animals and comparing the results with those obtained with known anorexigenic agents.

Oral Dose Route

Female $CF_1$ mice, which had been fasted for 17 to 21 hours, were dosed orally with the test compound (ten or more mice per dose). One-half hour later, each mouse was transferred to an individual compartment (13.3 cm × 12.7 cm × 12.7 cm) with a 0.64 cm × 0.64 cm wire mesh floor. Inside each compartment was a brass bar (13 cm × 1.2 cm × 1.2 cm) in the top of which were ten shallow, round spot depressions (0.8 cm diameter). Each depression contained 0.05 ml of 50% sweetened condensed milk.

Thirty minutes after the mice were transferred into the compartments, the number of milk spots each mouse had consumed was counted. Fractions of spots consumed also were estimated and counted. The percent anorexigenic effect was estimated by comparison of the mean number of spots of milk consumed per mouse at a given dose with the mean number of spots consumed per vehicle-treated control mouse. Dose-response curves were plotted and from these the ED50%, the dose at which treated mice would be expected to consume 50% as much milk as control mice, was calculated.

Subcutaneous Dose Route

Male $CF_1$ mice, which had been fasted for 17 to 21 hours, were dosed subcutaneously with the test compound (20 mice per dose) and placed into an individual compartment (13.3 cm × 12.7 cm × 12.7 cm) with a 0.64 cm × 0.64 cm wire mesh floor. 7½ to 15 minutes later a black Lucite bar (13 cm × 1.2 cm × 1.2 cm) in the top of which were ten shallow round spot depressions (0.8 cm diameter) was inserted into each compartment. Each depression contained 0.05 ml of 50% sweetened condensed milk.

Ten minutes after the milk was presented to the mice, the number of milk spots each mouse had consumed was counted. Fractions of spots consumed also were estimated and counted. Dose-response curves were plotted and from these the ED50%, the dose at which treated mice would be expected to consume 50% as much milk as control mice, was calculated.

In Table I, the oral ED50% values of compounds of this invention are compared with those for other anorexigenic agents.

TABLE I

| Compound | ED50% (mg/kg) | |
|---|---|---|
| | Oral | Subcutaneous |
| Example 1 | 2.5 | — |
| Example 2 | 84 | 3.2 |
| Naltrexone | 3.0 | 0.4 |
| Fenfluramine | 13.5 | 7.6 |

Since the compounds of Examples 1 and 2 cause decreased food intake in mice, it is expected that they will be suitable for the treatment of obesity in humans.

The active ingredient can be administered orally in solid dosage forms, such as capsules, tablets, and powders, or in liquid dosage forms, such as elixirs, syrups, and suspensions. The active ingredient can also be administered parenterally in suitable liquid dosage forms.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired.

The dose which would constitute an anorexigenically effective dose in a given mammal would be readily determined by one skilled in the art. Based upon the data set forth in the table, the human oral or parenteral dose of a compound of Example 1 or 2 for use as an anorectic is, according to this invention, about 20 to 200 mg per day, preferably 40 mg given 3 or 4 times daily or 120–160 mg total daily dose.

The following provides an example of a suitable dosage form. Equivalent materials and techniques may be used also.

| | |
|---|---|
| Compound of Example 1 | 40 mg/tablet |
| Lactose, U.S.P. | 230 mg/tablet |
| Microcrystalline Cellulose, N.F. | 23 mg/tablet |
| Stearic acid | 7 mg/tablet |

The compound of Example 1, lactose and microstalline cellulose are passed through a fine mesh screen and blended thoroughly. Stearic acid is then added to the mixture which is blended until homogeneous. The blended mixture is compressed into tablets weighing 300 mg each.

What is claimed is:

1. An appetite suppression composition comprising an effective appetite suppressing amount of a compound of Formula I:

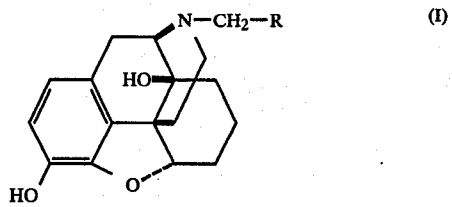

wherein R is cyclopropyl or cyclobutyl; or a pharmaceutically suitable salt thereof together with suitable vehicles and/or excipients therefor.

2. The appetite suppression composition of claim 1 wherein R is cyclopropyl.

3. The appetite suppression composition of claim 2 wherein the cyclopropyl-substituted compound of Formula I is present as the hydrochloride salt.

4. A method of suppressing appetite in a mammal which comprises administering to said mammal an effective appetite suppressing dose of the composition of claim 1.

5. The method of claim 4 wherein R is cyclopropyl.

6. The method of claim 4 wherein the cyclopropyl-substituted compound of Formula I is present as the hydrochloride salt.

7. The method of claim 4 wherein said mammal is a human being.

8. The method of claim 5 wherein said mammal is a human being.

9. A method for suppressing appetite in a mammal which comprises administering to said mammal an effective appetite suppressing dose of a compound of Formula I:

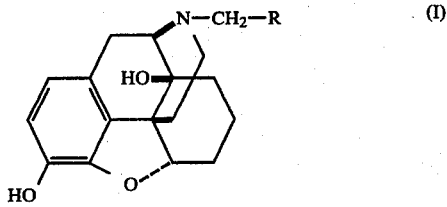

wherein R is cyclopropyl or cyclobutyl; or a pharmaceutically suitable salt thereof.

10. The method of claim 9 wherein R is cyclopropyl.

11. The method of claim 9 wherein the cyclopropyl-substituted compound of Formula I is present as the hydrochloride salt.

12. The method of claim 9 wherein said mammal is a human being.

* * * * *